(12) United States Patent
Belardinelli et al.

(10) Patent No.: US 9,125,916 B2
(45) Date of Patent: *Sep. 8, 2015

(54) METHODS OF TREATING HYPERTROPHIC CARDIOMYOPATHY

(71) Applicant: Gilead Sciences, Inc., Foster City, CA (US)

(72) Inventors: Luiz Belardinelli, Palo Alto, CA (US); Ramin Farzaneh-Far, Redwood City, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/444,796

(22) Filed: Jul. 28, 2014

(65) Prior Publication Data

US 2015/0038487 A1 Feb. 5, 2015

Related U.S. Application Data

(60) Provisional application No. 61/861,359, filed on Aug. 1, 2013.

(51) Int. Cl.
*A61K 31/553* (2006.01)
*A61K 31/506* (2006.01)

(52) U.S. Cl.
CPC ............. *A61K 31/553* (2013.01); *A61K 31/506* (2013.01)

(58) Field of Classification Search
CPC .................................................... A61K 31/553
USPC ................................................... 514/211.05
See application file for complete search history.

(56) References Cited

U.S. PATENT DOCUMENTS 8,586,732 B2 * 11/2013 Corkey et al. ................. 540/490
8,697,863 B2 * 4/2014 Elzein et al. .................. 540/490
2013/0184255 A1 * 7/2013 Corkey et al. ............. 514/211.05

FOREIGN PATENT DOCUMENTS

WO WO-2013/006485 A1 1/2013

OTHER PUBLICATIONS

Coppini et al. (2012) "Late Sodium Current Inhibition Reverses Electromechanical Dysfunction in Human Hypertrophic Cardiomyopathy" *Circulation AHA*, vol. 127:5. pp. 575-584.
International Search Report-Written Opinion dated Oct. 17, 2014 for PCT/US2014/048495.

* cited by examiner

*Primary Examiner* — Bruck Kifle
(74) *Attorney, Agent, or Firm* — Francis O. Ginah

(57) ABSTRACT

The present disclosure relates to a compound of formula (I) or formula (II)

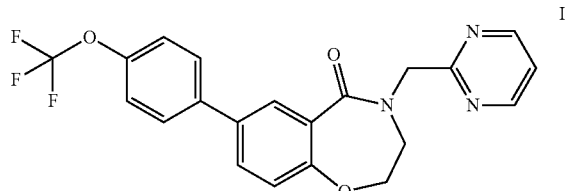

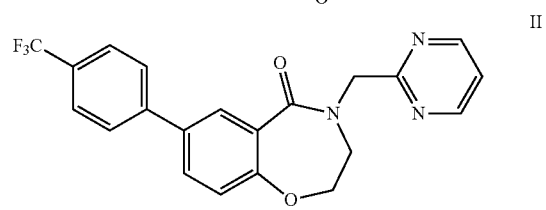

or a pharmaceutically acceptable salt thereof, for use in the treatment of hypertrophic cardiomyopathy.

10 Claims, No Drawings

METHODS OF TREATING HYPERTROPHIC CARDIOMYOPATHY

CROSS-REFERENCE TO RELATED APPLICATIONS

This application claims benefit under 35 U.S.C. §119(e) to U.S. Provisional Application Ser. No. 61/861,359, filed on Aug. 1, 2013, the entirety of which is incorporated herein by reference.

FIELD

The present disclosure relates to a method of treating hypertrophic cardiomyopathy (HCM).

BACKGROUND

Hypertrophic cardiomyopathy (HCM) is a genetic disease in which the heart muscle (myocardium) becomes abnormally thick (hypertrophied). This thickening of the muscle can make it harder for the heart to relax and pump blood efficiently. Hypertrophic cardiomyopathy may also affect the heart's electrical system resulting in arrhythmias. HCM is the most common genetic cardiac disease, affecting approximately 1 in 500 people. It is caused by autosomal-dominant mutations in genes encoding components of the cardiac sarcomere. HCM is recognized clinically as unexplained left ventricular (LV) hypertrophy (typically ≥15 mm thickness of the ventricular wall) in the absence of other cardiac or systemic conditions capable of producing the magnitude of hypertrophy observed. Typical symptoms include shortness of breath, angina, palpitations, fatigue and syncope. In a small percentage of patients, sudden cardiac death may be the first presentation. HCM is a leading cause of sudden cardiac death in young adults.

There are currently no approved drugs for the treatment of HCM. Empirical medical therapy is considered first-line and is based on using drugs that decrease cardiac contractility including for example, beta-blockers, calcium channel blockers and disopyramide, but their use is limited by lack of efficacy and/or poor tolerability.

Coppini et al. have established a key role for the cardiac late sodium current ($I_{Na,L}$) in the pathogenesis of HCM. In a study of human cardiac tissue derived from patients with symptomatic HCM undergoing septal myectomy (see Coppini et al, *Circulation* 2013; 127 (5):575-584), inhibition of late $I_{Na}$ with ranolazine was found to reverse multiple electrical and mechanical abnormalities characteristic of the disease.

One example of an inhibitor of $I_{Na,L}$ is RANEXA®, a compound approved by the FDA for the treatment of chronic stable angina pectoris. RANEXA® has also been shown to be useful for the treatment of a variety of cardiovascular diseases, including ischemia-reperfusion injury, arrhythmia and unstable angina, and also for the treatment of diabetes. It would be desirable to provide compounds and methods for treating HCM via selectively inhibit (INaL) in mammals and that have a similar or improved selectivity over peak INa inhibition of the cardiac sodium channel as compared with RANEXA®.

SUMMARY

The present disclosure provides a method for treating hypertrophic cardiomyopathy comprising administering of formula (I) or II:

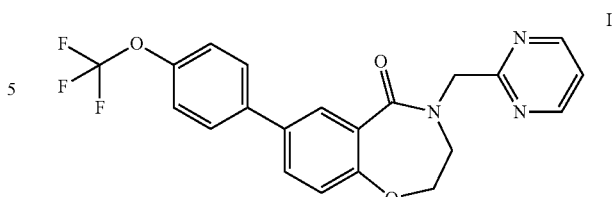

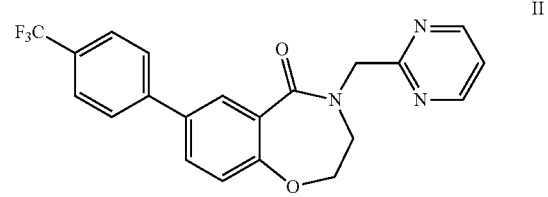

or a pharmaceutically acceptable salt thereof to a human patient in need thereof.

In another embodiment, the present disclosure provides a method of treating hypertrophic cardiomyopathy comprising administering a compound of formula (I) or (II):

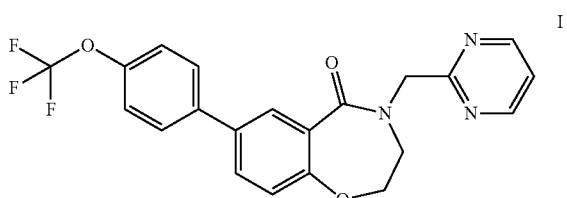

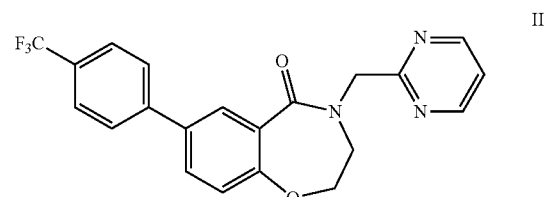

to a human patient in need thereof.

The present disclosure provides a method for treating hypertrophic cardiomyopathy comprising administering a compound of formula (I):

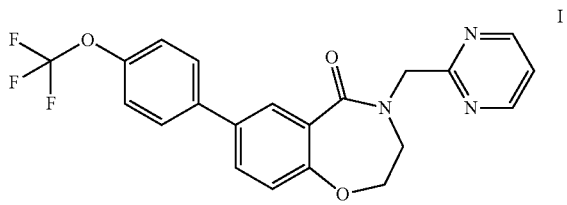 [SMILES: O=C1c2cc(-c3ccc(OC(F)(F)F)cc3)ccc2OCCN1Cc1ncccn1]

or a pharmaceutically acceptable salt thereof to a human patient in need thereof.

In another embodiment, the present disclosure provides a method of treating hypertrophic cardiomyopathy comprising administering a compound of formula (I):

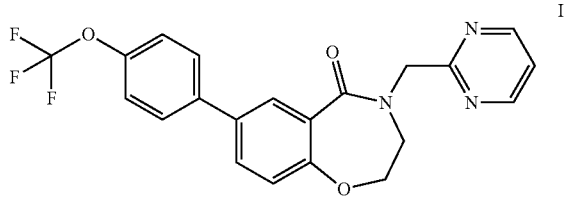 [SMILES: O=C1c2cc(-c3ccc(OC(F)(F)F)cc3)ccc2OCCN1Cc1ncccn1]

to a human patient in need thereof.

In another embodiment, the present disclosure provides a method for treating HCM comprising administering a compound of formula (II):

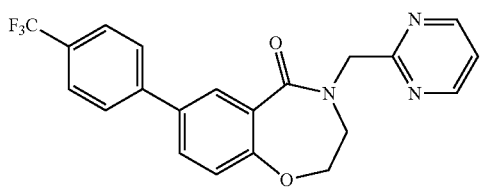

or a pharmaceutically acceptable salt thereof, to a human patient in need thereof.

In another embodiment, the present disclosure provides a method for treating HCM comprising administering a compound of formula (II):

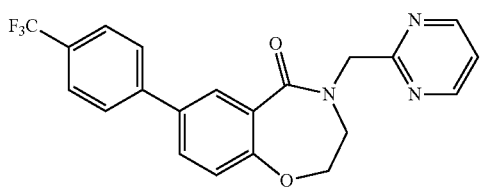

to a human patient in need thereof.

In another embodiment, the present disclosure provides the use of a compound of formula (I) or a pharmaceutically acceptable salt thereof, in the manufacture of a medicament for treating hypertrophic cardiomyopathy.

In another embodiment, the present disclosure provides a method of treating HCM wherein the compound of formula (I) or (II) is administered in a dose regimen comprising:
a. a loading dose on the first day of treatment, and
b. a daily maintenance dose thereafter.

In another embodiment, the present disclosure provides for the use of the compound of formula (I) or (II) in the preparation of a medicament for treating HCM wherein the compound of formula (I) or (II) is administered in a dose regimen comprising:
a. a loading dose on the first day of treatment, and
b. a daily maintenance dose thereafter.

In another embodiment, the present disclosure provides a method of treating HCM wherein the compound of formula (I) is administered in a dose regimen comprising:
a. a loading dose on the first day of treatment, and
b. a daily maintenance dose thereafter.

In another embodiment, the present disclosure provides for the use of the compound of formula (I) in the preparation of a medicament for treating HCM wherein the compound of formula (I) is administered in a dose regimen comprising:
a. a loading dose on the first day of treatment, and
b. a daily maintenance dose thereafter.

In another embodiment, the present disclosure provides the use of compound of formula (I) or (II) or a pharmaceutically acceptable salt thereof, in the manufacture of a medicament for treating hypertrophic cardiomyopathy.

In one embodiment of the disclosure, the loading dose of a compound of formula (I) or (II) is 30 mg and the maintenance dose is 3 mg or 6 mg.

The compounds of the present disclosure were disclosed in PCT International publication WO2013/006485 and U.S. Publication No. U.S.2013/0184255A1. However, the disclosures therein did not include a teaching or suggestion for use of the compound of formula (I) or (II) for the treatment of HCM.

The compounds of the present disclosure have been shown to be more potent than Ranexa® and are believed to present a first opportunity for the efficacious treatment of HCM.

DETAILED DESCRIPTION

1. Definitions and General Parameters

As used in the present specification, the following words and phrases are generally intended to have the meanings as set forth below, except to the extent that the context in space.

The term "therapeutically effective amount" refers to an amount of the compound of the disclosure that is sufficient to effect treatment, as defined below, when administered to a mammal in need of such treatment. The therapeutically effective amount will vary depending upon the, the weight and age of the subject, the severity of the disease condition, the manner of administration and the like, which can readily be determined by one of ordinary skill in the art.

The term "treatment" or "treating" means administration of a compound of the disclosure, by or at the direction of a competent caregiver, to a mammal, particularly a human, having a disease for purposes including:
(i) preventing the disease, that is, causing the clinical symptoms of the disease not to develop;
(ii) inhibiting the disease, that is, arresting the development of clinical symptoms; and/or
(iii) relieving the disease, that is, causing the regression of clinical symptoms.

The term "pharmaceutically acceptable salt" of a given compound refers to salts that retain the biological effectiveness and properties of the given compound, and which are not biologically or otherwise undesirable. Pharmaceutically acceptable base addition salts can be prepared from inorganic and organic bases. Salts derived from inorganic bases include, by way of example only, sodium, potassium, lithium, ammonium, calcium and magnesium salts. Salts derived from organic bases include, but are not limited to salts of primary, secondary and tertiary amines, such as alkyl amines, dialkyl amines, trialkyl amines, substituted alkyl amines, di(substituted alkyl) amines, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

As used herein, "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

Arrhythmia refers to any abnormal heart rate. Bradycardia refers to abnormally slow heart rate whereas tachycardia refers to an abnormally rapid heart rate. As used herein, the treatment of arrhythmia is intended to include the treatment of supraventricular tachycardias such as atrial fibrillation, atrial flutter, AV nodal reentrant tachycardia, AV reentrant tachycardia, atrial tachycardia and the ventricular tachycardias (VTs), including idiopathic ventricular tachycardia, ventricular fibrillation (VF), Torsades de Pointes (TdP), and pre-excitation syndromes 2. Nomenclature Naming for the compound of the present disclosure is provided using ACD/Name software for naming chemical compounds (Advanced Chemistry Development, Inc., Toronto, Canada). Other compounds or radicals may be named with common names or systematic or non-systematic names.

The compound of formula (I) of the disclosure is

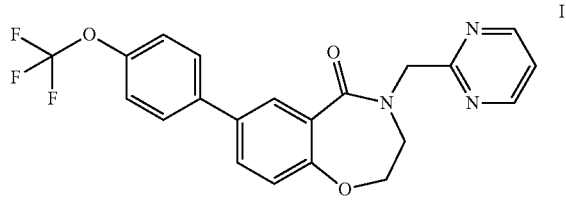 [SMILES: O=C1c2cc(-c3ccc(OC(F)(F)F)cc3)ccc2OCCN1Cc1ncccn1]

named 4-(pyrimidin-2-ylmethyl)-7-(4-(trifluoromethoxy)phenyl)-3,4-dihydrobenzo[f][1,4]oxazepin-5(2H)-one.

The compound of formula (I) of the present disclosure is prepared as disclosed in Example 1, below, and as described in WO2013/006485 and in U.S. 2013/0012492, the entirety of which is incorporated herein by reference. The compound of formula (II) is also prepared by use of the trifluoromethyl phenyl analog of the trifluoromethyl phenyl boronic acid source used in example 1. One of skill is aware deuterated analogs of the compounds of the disclosure may be prepared for use in the treatment of HCM using methods known in the art. Thus, the deuterated analog of the compound of formula (I) is also an embodiment of the present disclosure.

3. Pharmaceutical Compositions and Administration

The compounds of the present disclosure may be administered in the form of pharmaceutical compositions. This disclosure therefore provides pharmaceutical compositions that contain, as the active ingredient, the compound of formula (I) or formula (II), or a pharmaceutically acceptable salt thereof, and one or more pharmaceutically acceptable excipients, carriers, including inert solid diluents and fillers, diluents, including sterile aqueous solution and various organic solvents, permeation enhancers, solubilizers and adjuvants. The pharmaceutical compositions may be administered alone or in combination with other therapeutic agents. Such compositions are prepared in a manner well known in the pharmaceutical art (see, e.g., Remington's Pharmaceutical Sciences, Mace Publishing Co., Philadelphia, Pa. 17th Ed. (1985); and Modern Pharmaceutics, Marcel Dekker, Inc. 3rd Ed. (G. S. Banker & C. T. Rhodes, Eds.)

The pharmaceutical compositions may be administered in either single or multiple doses by any of the accepted modes of administration of agents having similar utilities, for example as described in those patents and patent applications incorporated by reference, including rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

One mode for administration is parenteral, particularly by injection. The forms in which the novel compositions of the present disclosure may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles. Aqueous solutions in saline are also conventionally used for injection, but less preferred in the context of the present disclosure. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating a compound according to the present disclosure in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. Preferably, for parenteral administration, sterile injectable solutions are prepared containing a therapeutically effective amount, e.g., 0.1 mg to 700 mg, of a compound described herein. It will be understood, however, that the amount of the compound actually administered usually will be determined by a physician, in the light of the relevant circumstances, including the condition to be treated, the chosen route of administration, the actual compound administered and its relative activity, the age, weight, and response of the individual patient, the severity of the patient's symptoms, and the like.

Oral administration is another route for administration of the compound in accordance with the present disclosure. Administration may be via capsule or enteric coated tablets, or the like. In making the pharmaceutical compositions that include a compound described herein, the active ingredient is usually diluted by an excipient and/or enclosed within such a carrier that can be in the form of a capsule, sachet, paper or other container. When the excipient serves as a diluent, it can be in the form of a solid, semi-solid, or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl and propylhydroxy-benzoates; sweetening agents; and flavoring agents.

The compositions of the disclosure may be formulated so as to provide quick, sustained or delayed release of the active ingredient after administration to the patient by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods of the present disclosure employs transdermal delivery devices ("patches"). Such transdermal patches may be used to provide continuous or discontinuous infusion of the compounds of the present disclosure in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

The compositions are preferably formulated in a unit dosage form. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient (e.g., a tablet, capsule, ampoule). The compounds are generally administered in a pharmaceutically effective amount Preferably, for oral administration, each dosage unit contains from 1 mg to 2 g, or alternatively, or 100 mg to 500 mg, of a compound described herein, and for parenteral administration, preferably from 0.1 mg to 700 mg, or alternatively, 0.1 mg to 100 mg, of a compound described herein. Another embodiment for the practice of the present disclosure comprises a dosing regimen that comprises (1) a loading dose and (2) a maintenance dose. In another embodiment the initial administration will be a single loading dose of from about 20 mg to about 50 mg on the first day (and optionally on days 2 and/or 3) followed by a daily maintenance dose from about 3 mg to about 10 mg. In yet another embodiment, the practice of the disclosure comprises an initial loading dose of about 30 mg on the first day followed by a daily maintenance dose of about 3 mg or about 6 mg. In another embodiment, the initial administration will be a loading regimen of about 6 mg or about 12 mg given twice daily for up to 7 days followed by a daily maintenance dose of about 3 mg or about 6 mg. In another embodiment, the qualified caregiver is able to tailor a dose regimen to fit with the particular needs of the patient. Thus, it will be understood that the amount of the compound of the disclosure actually administered usually will be determined by a physician, in the light of the relevant circumstances, including the condition(s) to be treated, the chosen route of administration, the actual compound (e.g. salt or free base) administered and its relative activity, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present disclosure. When referring to these preformulation compositions as homogeneous, it is meant that the active ingredient is dispersed evenly throughout the composition so that the composition may be readily subdivided into equally effective unit dosage forms such as tablets, pills and capsules.

The tablets or pills of the present disclosure may be coated or otherwise compounded to provide a dosage form affording the advantage of prolonged action, or to protect from the acidic condition of the stomach. For example, the tablet or pill can comprise an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably, the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a facemask tent, or intermittent positive pressure breathing machine. Solution, suspension, or powder compositions may be administered, preferably orally or nasally, from devices that deliver the formulation in an appropriate manner.

EXAMPLES

The following example is included to demonstrate preferred embodiments of the disclosure. It should be appreciated by those of skill in the art that the techniques disclosed in the examples which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

| List of abbreviations and acronyms. | |
|---|---|
| Abbreviation | Meaning |
| °C. | Degree Celsius |
| conc. | Concentrated |
| d | Doublet |

List of abbreviations and acronyms.

| Abbreviation | Meaning |
|---|---|
| dd | Doublet of doublets |
| DMF | Dimethylformamide |
| dppf | 1,1'-Bis(diphenylphosphino)ferrocene |
| equiv/eq | Equivalents |
| Et | Ethyl |
| g | Grams |
| h | Hours |
| Hz | Hertz |
| iPr | isopropyl |
| J | Coupling constant |
| Kg | Kilogram |
| LCMS/LC-MS | Liquid chromatography-mass spectrometry |
| M | Molar |
| m | multiplet |
| m/z | mass-to-charge ratio |
| M+ | Mass peak |
| M + H | Mass peak plus hydrogen |
| Me | Methyl |
| mg | Milligram |
| MHz | Megahertz |
| mM | Millimolar |
| mol | mole |
| MS | Mass spectroscopy |
| ms | Millisecond |
| N | Normal |
| mol | Mole |
| NMR | Nuclear magnetic resonance |
| RT/rt | Room temperature |
| s | Second |
| t | Triplet |
| THF | Tetrahydrofuran |
| δ | Chemical shift |
| μL/μl | Microliter |
| μM | Micromolar |

EXAMPLE

Example 1

4-(pyrimidin-2-ylmethyl)-7-(4-(trifluoromethoxy)phenyl)-3,4-dihydrobenzo[f][1,4]oxazepin-5(2H)-one (Compound I)

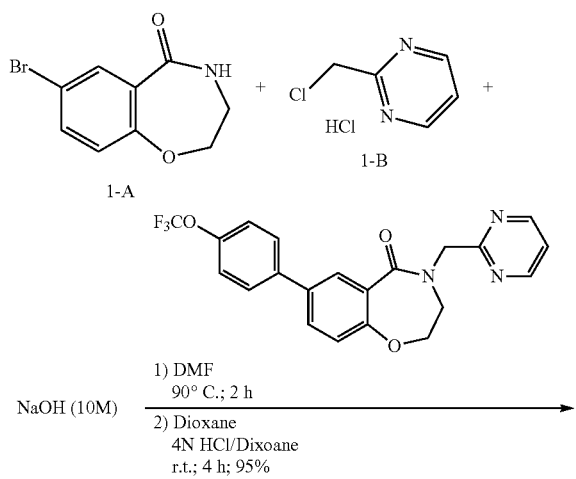

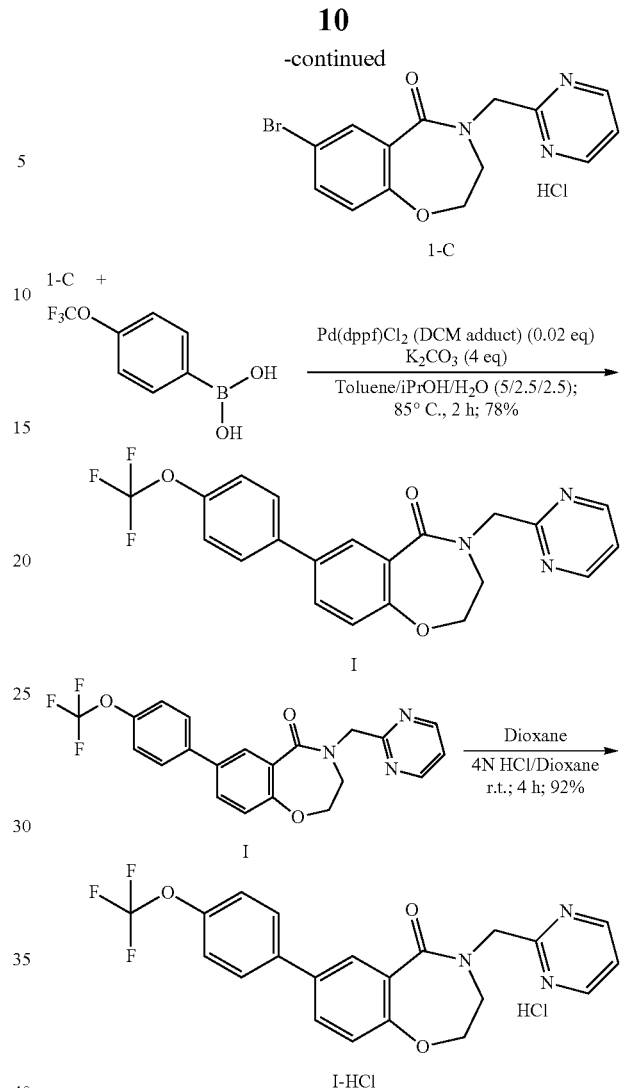

To a solution of Compound 1-A (20 g, 0.083 mol, 1 eq.) and Compound 1-B (25 g, 0.15 mol, 1.8 eq.) in DMF (150 mL), NaOH solution (20 mL, 10 M, 5 eq.) was slowly added at room temperature (slightly exothermic) and stirred at r.t. for 10 min, followed by heating at 95° C. for 2 h. After cooling the reaction mixture, ethyl acetate (200 mL) was added and the organic layer was separated. The organics was washed with water (20 mL), brine, dried over sodium sulphate and concentrated.

The residue was dissolved in 1,4-dioxane (50 mL) and to this 4 N HCl in dioxane (50 mL) and conc. HCl (2 mL) was added and stirred at room temperature for 4 h, filtered the precipitate, washed with ethyl acetate and dried. Compound 1-C was obtained (30 g) as a light yellow solid.

To the bromide (15 g, 0.04 mol, 1 eq), boronic acid (12.5 g, 0.06 mol, 1.5 eq) and potassium carbonate (22 g, 0.16 mol, 4 eq) in a round bottom flask, solvent (150 mL, toluene/isopropanol/water: 2/1/1) was added and stirred under nitrogen for 10 min. To the above solution the palladium catalyst (1 g, 0.012 mol, 0.02 eq) was added and heated at 85° C. for 2 h. The reaction mixture was diluted with ethyl acetate, separated the organic layer and filtered the organic layer through a plug of celite and silica gel and concentrated. Column purification on silica gel using ethyl acetate/hexane as eluent provided Compound I (13 g).

To a solution of Compound I (26 g) in 1,4-dioxane (25 mL), 4N HCl/dioxane (25 mL) was added followed by conc. HCl (2 mL) and stirred at room temperature for 4 h. Solvent was distilled off, dichloromethane was added and distilled off and to the residue, ethyl acetate (150 mL) was added and stirred at room temperature overnight and filtered the precipitate, washed with ethyl acetate, hexane and dried under vacuum. Compound I—HCl obtained (24.8 g) was a white solid.

$^1$H-NMR (CDCl$_3$) δ 8.72 (d, 2H, J=5.2 Hz), 8.17 (d, 1H, J=2.4 Hz), 7.59-7.63 (m, 3H), 7.26 (d, 2H, J=3.2 Hz), 7.22 (t, 1H, J=4.8 Hz), 7.10 (d, 1H, J=8.4 Hz), 5.10 (s, 2H), 4.56 (t, 2H, J=5.0 Hz), 3.77 (t, 2H, J=5.0 Hz); MS m/z 416.1 (M+H).

Example 2

4-(pyrimidin-2-ylmethyl)-7-(4-(trifluoromethyl)phenyl)-3,4-dihydrobenzo[f][1,4]oxazepin-5(2H)-one

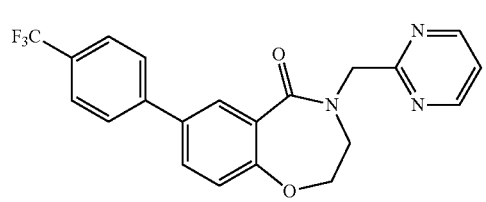

The compound of formula (II) is prepared following the process of Example 1 by substituting 4-trifluoromethyl phenylboronic acid in place of 4-trifluromethoxy phenyl boronic acid.

What is claimed is:

1. A method for treating hypertrophic cardiomyopathy comprising administering a compound of formula (I) or II:

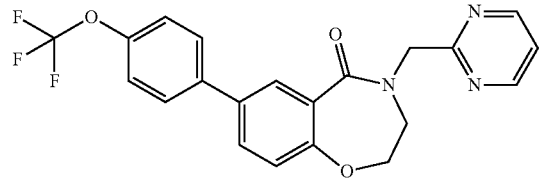

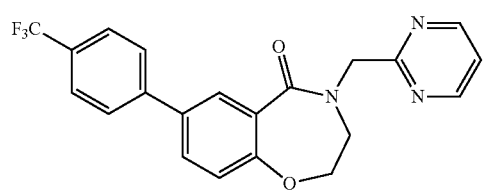

or a pharmaceutically acceptable salt thereof to a human patient in need thereof.

2. The method according to claim 1 for treating hypertrophic cardiomyopathy comprising administering a compound of formula (I) or II:

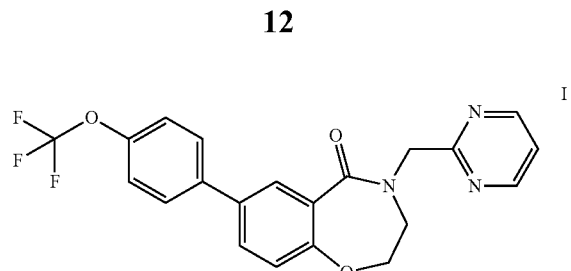

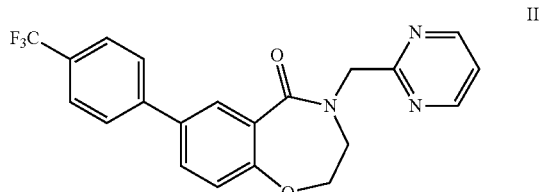

to a human patient in need thereof.

3. The method according to claim 1 comprising administering a compound of formula (I):

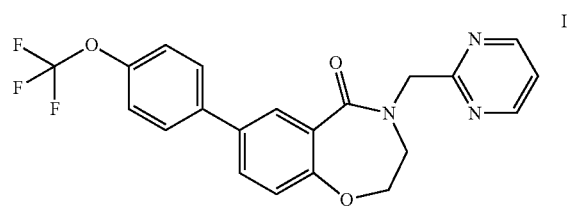 [SMILES: O=C1c2cc(-c3ccc(OC(F)(F)F)cc3)ccc2OCCN1Cc1ncccn1]

or a pharmaceutically acceptable salt thereof, to a human patient in need thereof.

4. The method according to claim 1 comprising administering a compound of formula (I):

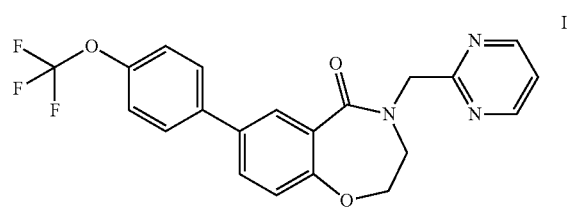 [SMILES: O=C1c2cc(-c3ccc(OC(F)(F)F)cc3)ccc2OCCN1Cc1ncccn1]

to a human patient in need thereof.

5. The method according to claim 1 comprising administering a compound of formula (II):

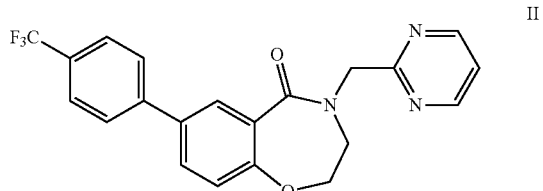

or a pharmaceutically acceptable salt thereof, to a human patient in need thereof.

6. The method according to claim 1 comprising administering a compound of formula (II):

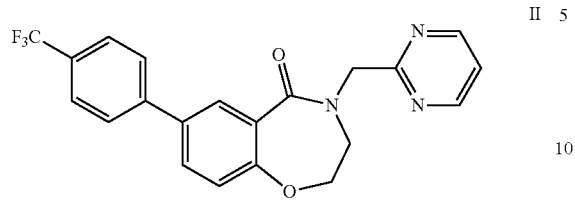

to a human patient in need thereof.

7. The method according to claim 1 wherein the Compound of formula (I) or (II) is administered in a dose regimen comprising:
   a. a loading dose on the first day of treatment, and
   b. a daily maintenance dose thereafter.

8. The method according to claim 7 wherein the loading dose is 30 mg.

9. The method according to claim 7 wherein the maintenance dose is 3 mg daily.

10. The method according to claim 7 wherein the maintenance dose is 6 mg daily.

* * * * *